United States Patent [19]

Kurn et al.

[11] Patent Number: 5,104,812

[45] Date of Patent: Apr. 14, 1992

[54] DEVICE AND METHOD FOR INTERRUPTING CAPILLARY FLOW

[75] Inventors: Nurith Kurn, Palo Alto; Rajesh D. Patel, Fremont; Martin Becker, Palo Alto; Edwin F. Ullman, Atherton, all of Calif.

[73] Assignee: Syntex (U.S.A.) Inc., Palo Alto, Calif.

[21] Appl. No.: 441,688

[22] Filed: Nov. 27, 1989

[51] Int. Cl.⁵ ............................................. G01N 33/52
[52] U.S. Cl. ..................................... 436/165; 436/170; 436/180; 436/807; 422/56; 422/58; 422/60; 422/61; 435/4; 435/805; 435/810
[58] Field of Search ................... 422/56, 60, 57, 58, 422/61; 436/161, 165, 169, 170, 180, 807, 810, 514; 435/4, 805, 808, 810

[56] References Cited

U.S. PATENT DOCUMENTS

| | | | |
|---|---|---|---|
| 3,482,943 | 12/1969 | Csizmas et al. | 422/58 X |
| 4,826,759 | 5/1989 | Guire et al. | 422/58 X |
| 4,839,297 | 6/1989 | Freitag et al. | 436/170 |
| 4,849,340 | 7/1989 | Oberhardt | 422/58 X |
| 4,857,453 | 8/1989 | Ullman et al. | 436/810 X |
| 4,883,764 | 11/1989 | Kloepfer | 436/170 X |

Primary Examiner—David L. Lacey
Assistant Examiner—Jeffrey R. Snay
Attorney, Agent, or Firm—Theodore J. Leitereg

[57] ABSTRACT

Disclosed are devices and methods for interrupting capillary flow of a liquid between two pieces of bibulous material which, prior to actuation, are in a capillary flow relationship to each other. In particular, the capillary flow relationship of two pieces of bibulous material is interrupted by utilizing a liquid expandable piece of bibulous material.

34 Claims, 5 Drawing Sheets

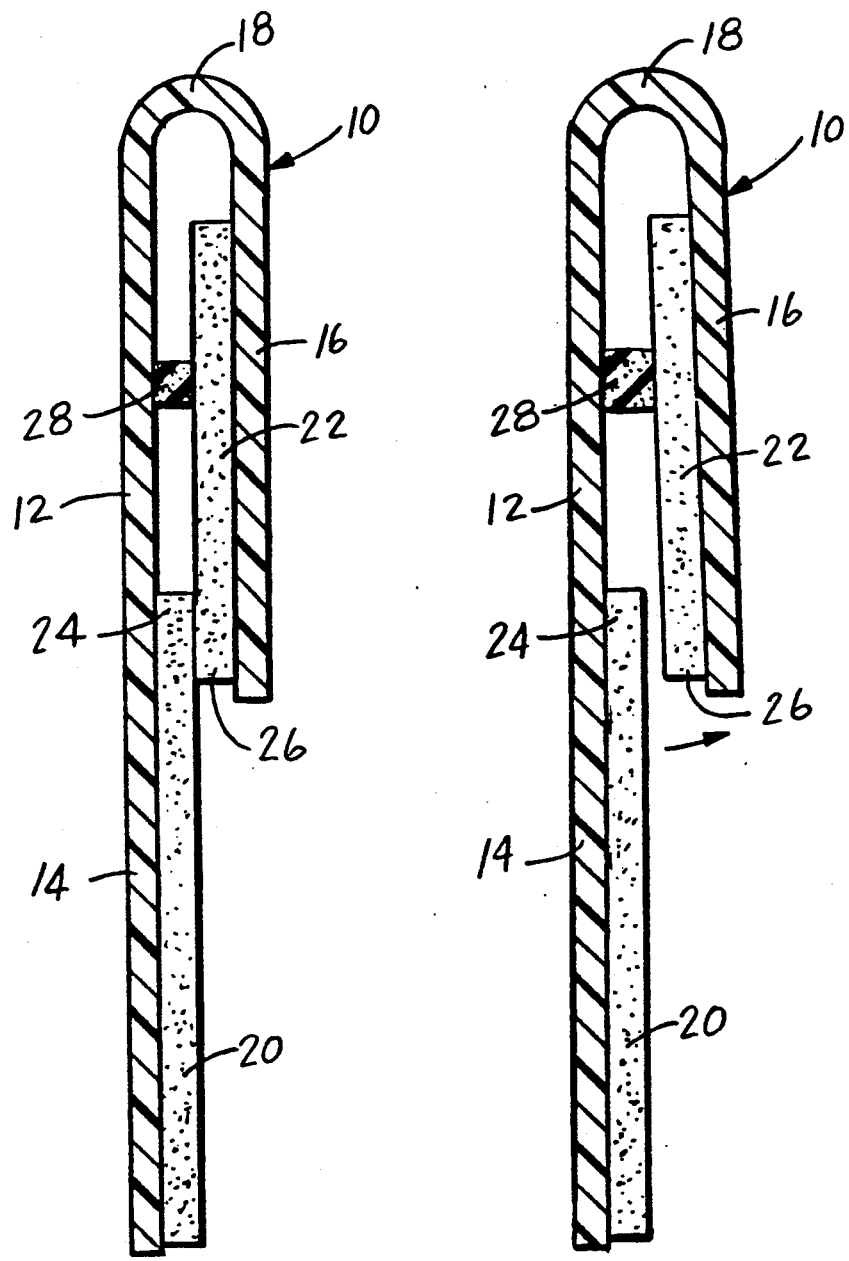
FIG._1A  FIG._1B

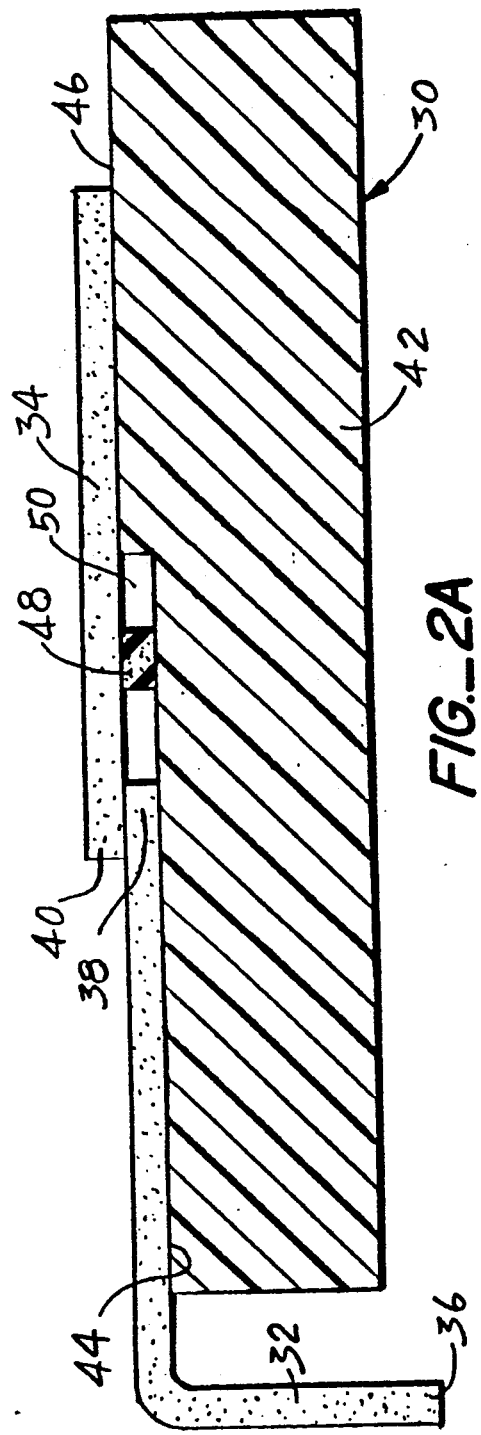
FIG._2A
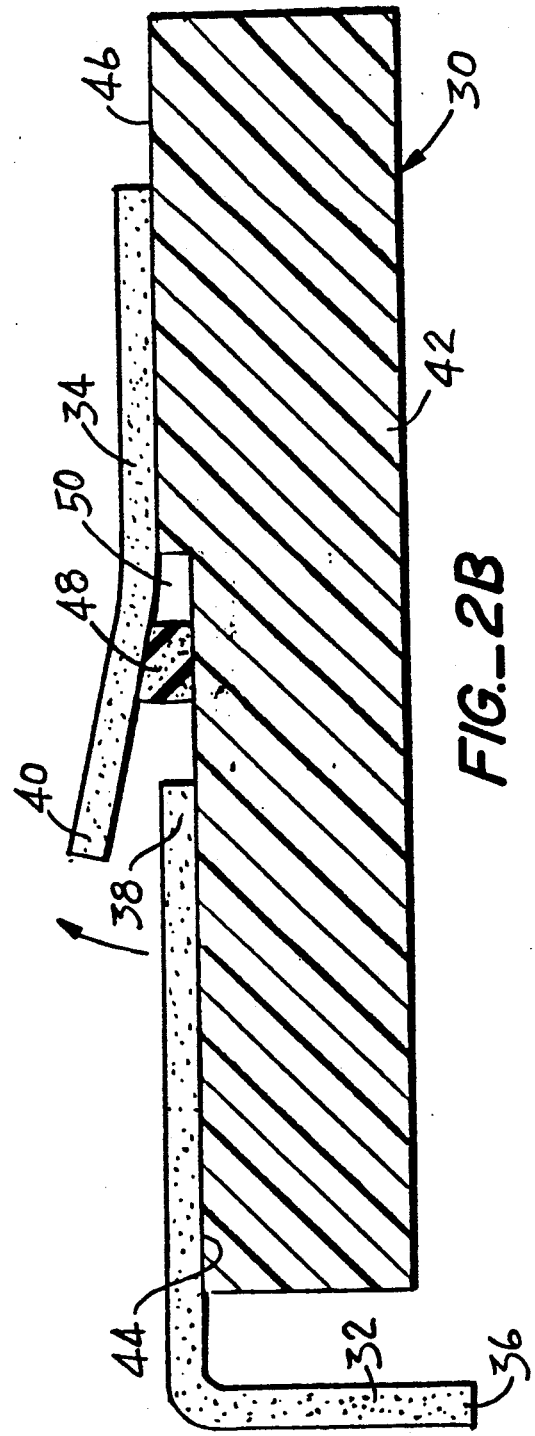
FIG._2B

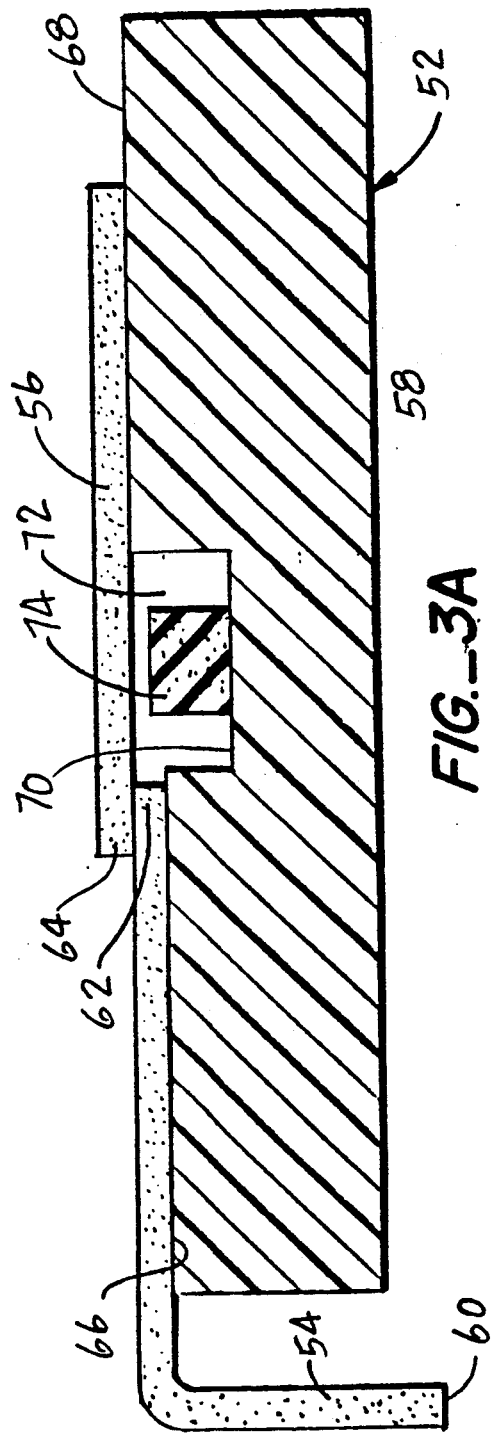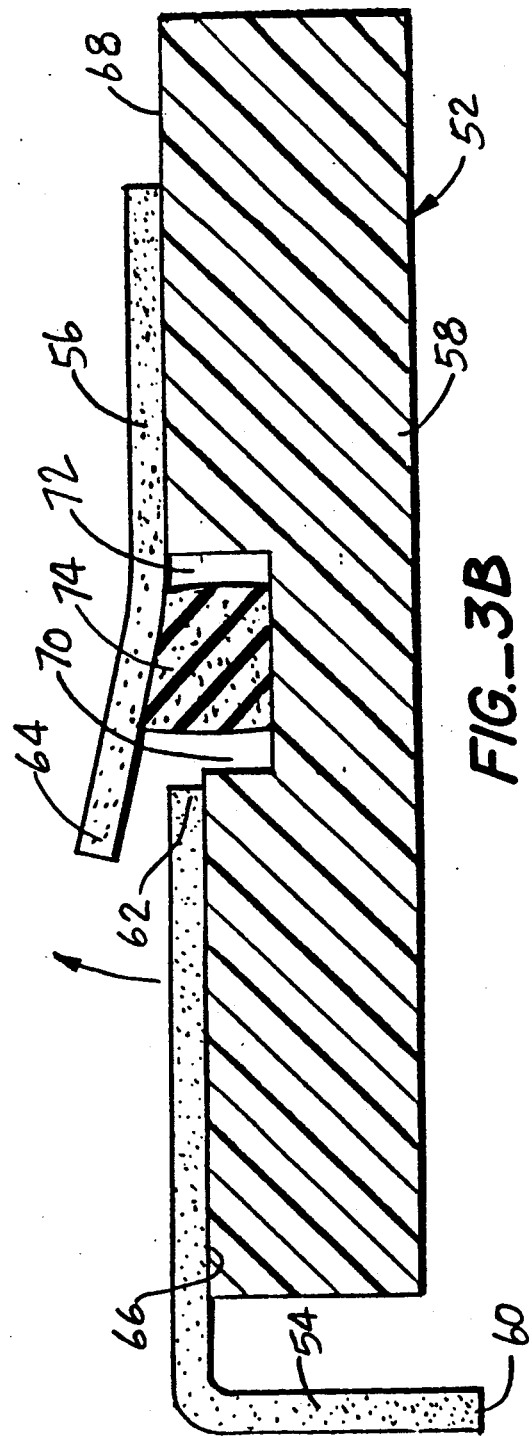

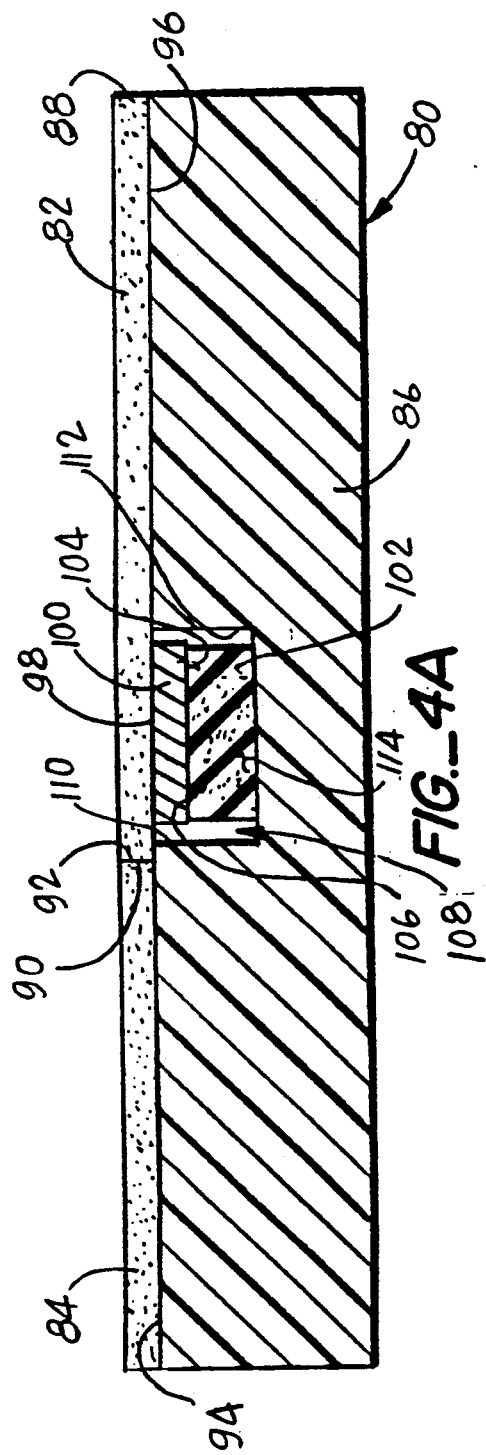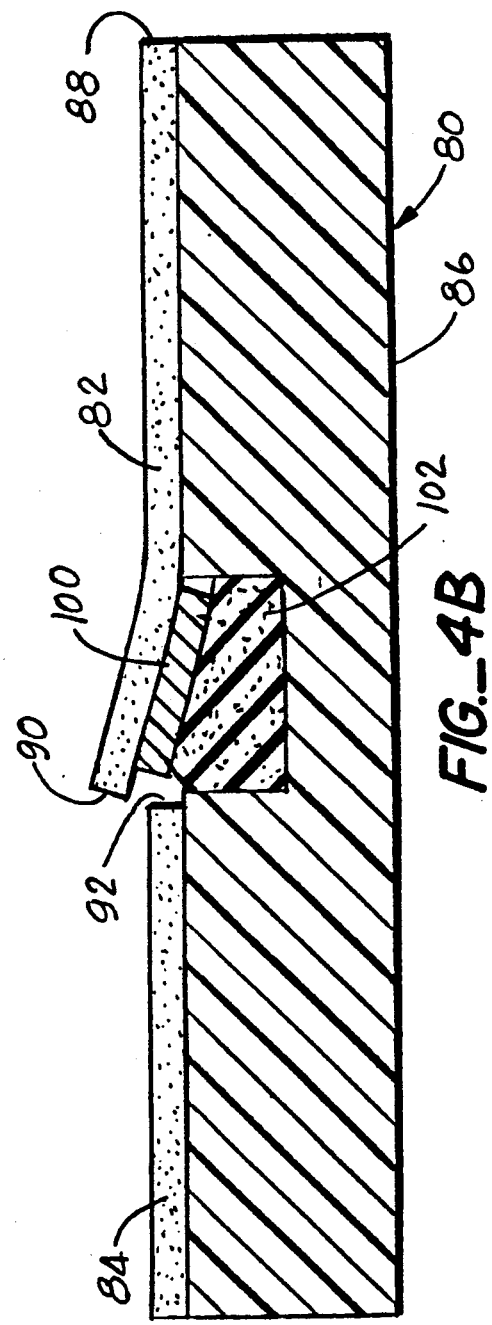

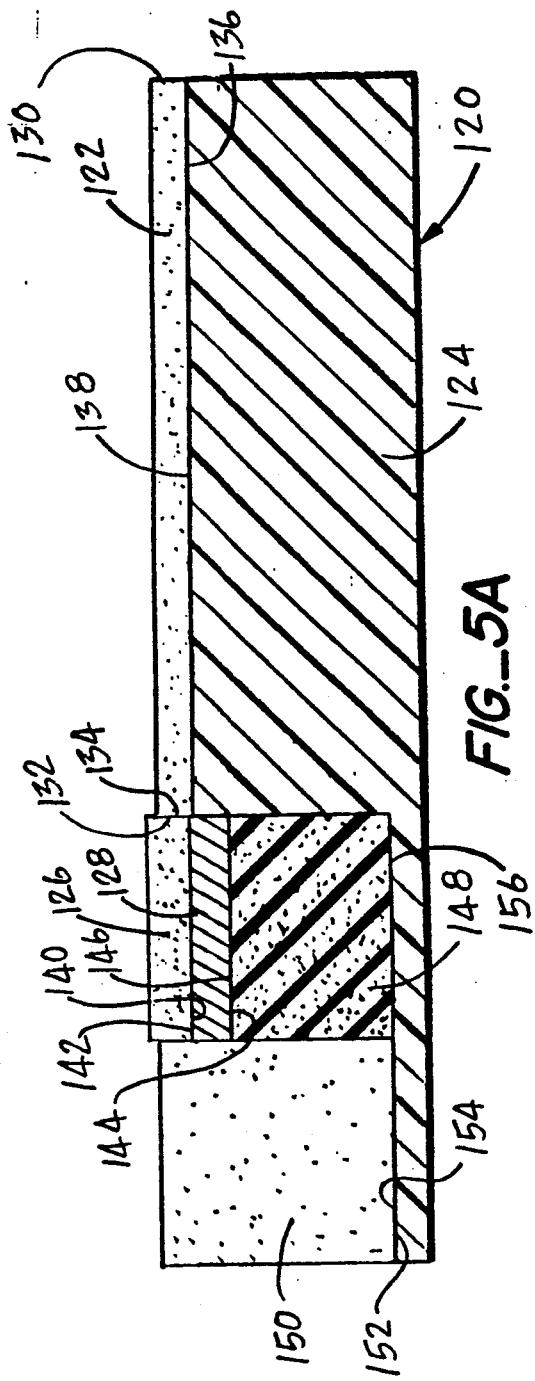
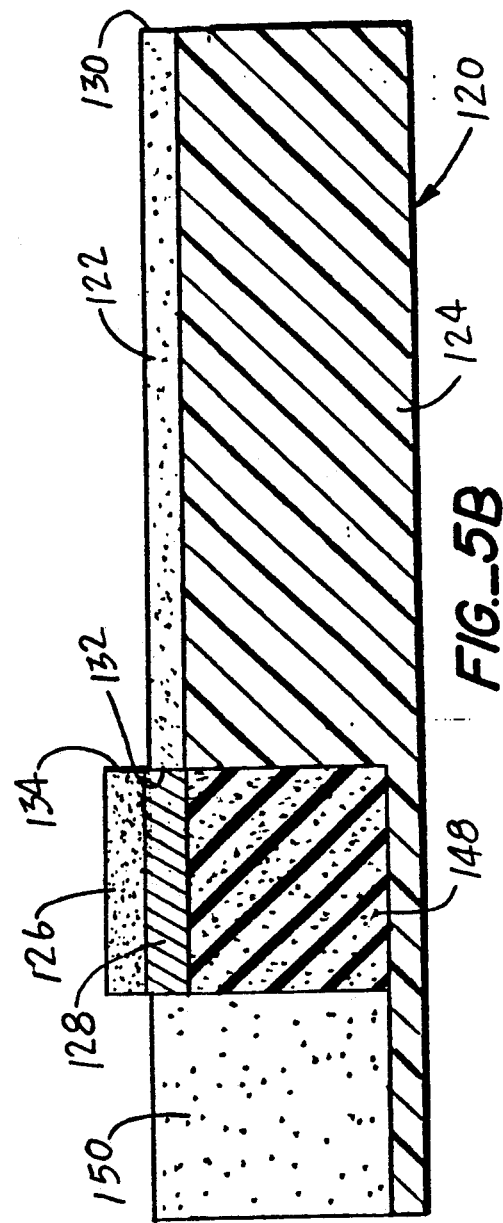

DEVICE AND METHOD FOR INTERRUPTING CAPILLARY FLOW

BACKGROUND OF THE INVENTION

1. Field of the Invention

The present invention is directed to devices and methods for interrupting capillary flow of liquid between two pieces of bibulous material which, prior to actuation, are in a capillary flow relationship to each other. In particular, the device is actuated and the capillary flow relationship between two pieces of bibulous material is interrupted by utilizing a liquid expandable piece of bibulous material. When actuated by wetting, the liquid expandable piece of bibulous material interrupts capillary flow between two pieces of bibulous material by separating these two pieces which interrupts their capillary flow relationship. The methods and devices of the present invention have particular utility in assays which require transport over set times or of set volumes of solutions and/or samples by capillarity. Such assays include, for example, enzyme immunoassays, fluorescent immunoassays, radioimmunoassays, etc.

2. Related Art

Assay devices have been described in which liquid is transported by capillarity through or transversely along a bibulous support thereby transporting reagents and samples to sites on the support and/or washing the support. Such devices have been described by Deutsch, U.S. Pat. No. 4,094,647; Zuk et al, U.S. Pat. No. 4,435,504; Weng et al, U.S. Pat. No. 4,740,468; Friesen et al, German Offenlengungschrift 3,445,816, etc.

In many of these methods, a specified amount of a liquid reagent is added to the bibulous support. In such situations, it is desirable for a liquid reagent moving along a bibulous support to automatically stop moving after the specified volume of this reagent has been taken up so as to avoid the necessity of monitoring the flow of this reagent.

In the past, the flow can be stopped by limiting the length of the bibulous material. However, this approach requires that assays utilizing different amounts of liquid reagent utilize different lengths of bibulous material (assuming of course that all the other variables, such as the thickness of the bibulous material, etc. are the same). However, use of different lengths of bibulous material is substantially less efficient than a system which controls the amount of liquid reagent added to the bibulous support regardless of its length because the latter would permit the use of standardized lengths of bibulous material in assays requiring uptake of different amounts of liquid reagents. Moreover, the use of standardize lengths of bibulous materials would permit the use of standardize devices such as that depicted in U.S. Ser. No. 35,562 now U.S. Pat. No. 4,857,453 filed on Apr. 7, 1987 entitled "Immunoassay Devices" which is incorporated herein in its entirety.

Accordingly, it is desirable to interrupt the capillary flow of liquid between two pieces of bibulous material which theretofore were in a capillary flow relationship to each other after a specified amount of reagent has been taken up by the pieces of bibulous material. Moreover, it would be particularly desirable to interrupt such a capillary flow relationship automatically without mechanical means external to the device while requiring little or no operator involvement.

U.S. Pat. No. 3,482,943 discloses expandable sponges useful in transporting solution to a set position on a gel suitable for conducting immunodiffusion tests. In this reference, the solution transported by the sponge is allowed to diffuse into the gel which, in order to conduct the immunodiffusion, is by necessity a wet gel. Accordingly, no capillary flow relationship between the expandable sponge and the gel is established by this device.

U.S. Pat. No. 4,246,339 discloses a device having an upper portion and a lower portion. The upper portion has a plurality of wells wherein the bottom of each well is fitted with a membrane layer capable of transporting liquid. The bottom portion of the device contains absorbent material. Between the top and bottom portions is a compressible spacer. This device allows a liquid sample to be added to the wells which may optionally be impregnated with an antibody. After a set incubation period, pressure is placed on the top portion which because of the compressible spacer, allows the bottom of each of the wells to contact the absorbent material whereupon the liquid in the wells is transferred to the absorbent material. After liquid transfer, the pressure is removed and contact between the bottom of the wells and the absorbent material is broken. Thereupon, additional liquid may be added to the wells. In this device, care must be taken to insure that the bottom of all of the wells come into contact with the absorbent material for a sufficient period of time to remove the liquid. In particular, if one or more of the wells does not contact the absorbent material, then the liquid in that well will not be removed. Moreover, if one or more of the wells does not contact the absorbent material for a sufficient period of time, then not all of the liquid in that well will be removed. In any case, a high level of operator care is required to ensure the proper operation of this device.

U.S. Ser. No. 35,562 filed Apr. 7, 1987 entitled "Immunoassay Devices" discloses a device for conducting an assay method. The device comprises a housing having in one portion thereof a breakable capsule and in another portion a piece of bibulous material attached to an absorbent pad. However, this reference neither teaches or suggests the use of a liquid expandable piece of bibulous material which, when desired, can interrupt capillary flow relationship between two pieces of bibulous material.

European Patent Application Publication No. 0 146 691 discloses an air bleed passage in a liquid sampling needle which is formed between a housing and a sleeve and into which is added a solid compacted material which swells on contact with liquid. As the liquid sample is drawn into the needle, air can escape via the air bleed until the air bleed is contacted with liquid whereupon it expands and forms a liquid impermeable membrane.

U.S. Pat. No. 4,700,741 discloses a urine collecting device which contains an expandable sponge in a compartment which permits the collection of a predetermined quantity of urine by limiting expansion of the sponge within the compartment.

Canadian Patent No. 1,185,882 discloses porous hydrophilic, non-gel-forming swellable polymers as self-drawing fluid reservoirs with a very high and uniform absorption and release of fluid in a chromatographic quick-test device.

U.S. Pat. No. 4,826,759 describes apparatuses and methods, which can be used in the field (i.e., outside the laboratory environment) to determine qualitatively and at least semiquantitatively the presence or absence of minute quantities of ligand. The apparatus can be in the form of a strip comprising a support means provided with a groove intermediate its ends forming a crease line upon which the strip can be folded upon itself with bibulous elements and spaced from the crease line and arranged so that when the strip is folded upon itself the bibulous elements become aligned with each other and come into liquid contact.

U.S. Pat. No. 4,803,170 discusses an immunoassay device including one or more reaction chambers, each adapted to receive and retain a volume of test fluid in fluid communication with nonoverlapping first, second, and third reagent-bearing surfaces. To the first surface is reversibly bound an analyte conjugate: analyte component conjugated to one or more components, termed ligand/marker, that serve ligand and marker functions as described herein. Analyte binding partner is immobilized on the second surface, and ligand/marker binding partner is immobilized on the third surface. The reaction chamber is preferably configured to receive and direct the test fluid sequentially past the first, second, and third reagent surfaces. In use, analyte conjugate solubilized from the first surface completes with any analyte in the test fluid for analyte binding partner sites on the second surface. Excess analyte conjugate becomes sequestered on the third surface, where the marker activity is read to indicate analyte presence and concentration in the test fluid. A test kit includes the immunoassay device in combination with comparative test results.

Accordingly, there is a need for a device for interrupting a capillary flow relationship between two pieces of bibulous material which prior to actuation are in a capillary flow relationship to each other. Preferably, such a device would automatically interrupt this capillary flow relationship after a specified amount of liquid has been taken up and would require little or no operator involvement to actuate.

SUMMARY OF THE INVENTION

The present invention is directed to devices and methods for interrupting capillary flow of liquid through two pieces of bibulous material which are in a capillary flow relationship to each other. In particular, in one of its device aspects, the present invention is directed to a device for interrupting capillary flow of a liquid between two pieces of bibulous material which prior to actuation are in a capillary flow relationship to each other which comprises (a) first and second pieces of bibulous material in a capillary flow relationship to each other; and (b) a liquid expandable piece of bibulous material.

In one of its method aspects the present invention is directed toward a method for interrupting capillary flow of a liquid between first and second pieces of bibulous material which prior to actuation are in a capillary flow relationship to each other. The method comprises contacting a portion of a first piece of bibulous material with a liquid, the portion being non-adjacent to a portion of a second piece of bibulous material wherein the first and second pieces of bibulous material, each having adjacent and non-adjacent portions. The adjacent portions are in capillary flow relationship to each other; next, the liquid is allowed to traverse by capillarity through at least a portion of the second piece of bibulous material. Then, liquid is allowed to actuate a liquid expandable piece of bibulous material whereupon the liquid expandable piece of bibulous material expands and forces the adjacent portions of the first and second pieces of bibulous material out of capillary flow relationship to each other.

In another of its method aspects, the present invention is directed toward a method for interrupting capillary flow of a liquid between first and second pieces of bibulous material which prior to actuation are in a capillary flow relationship to each other which comprises (a) providing a device which comprises (i) first and second pieces of bibulous material each having adjacent and non-adjacent portions wherein said adjacent portions are in capillary flow relationship to each other, and (ii) a liquid expandable piece of bibulous material; (b) contacting said non-adjacent portion of said first piece of bibulous material with a liquid and allowing said liquid to traverse by capillarity through at least a portion of said second piece of bibulous material; and (c) allowing liquid to actuate said liquid expandable piece of bibulous material whereupon said liquid expandable piece of bibulous material expands and forces said adjacent portions of said first and second pieces of bibulous material out of capillary flow relationship to each other.

BRIEF DESCRIPTION OF THE DRAWINGS

FIG. 1A is a cross-sectional view of one embodiment of this invention in its unactuated state; FIG. 1B is a cross-sectional view of the embodiment of FIG. 1A in its actuated state.

FIG. 2A is a cross-sectional view of another embodiment of the present invention in its unactuated state; FIG. 2B is a cross-sectional view of the embodiment of FIG. 2A in its actuated state.

FIG. 3A is a cross-sectional view of still another embodiment of the present invention in its unactuated state; FIG. 3B is a cross-sectional view of the embodiment of FIG. 3A in its actuated state.

FIG. 4A is a cross-sectional view of another embodiment of the present invention in its unactuated state; FIG. 4B is a cross-sectional view of the embodiment of FIG. 4A in its actuated state.

FIG. 5A is a cross-sectional view of another embodiment of the present invention in its unactuated state; FIG. 5B is a cross-sectional view of the embodiment of FIG. 5A in its actuated state.

DETAILED DESCRIPTION OF THE INVENTION

Devices are provided which permit the interruption of a capillary flow relationship between two pieces of bibulous material. In particular, the devices of the present invention are useful for interrupting a capillary flow relationship between two or more pieces of bibulous material which theretofore were in a capillary flow relationship to each other.

The devices of the present invention are adaptable to a wide variety of analytical uses which require interruption of an existing capillary flow relationship between two pieces of bibulous materials. The devices of the present invention are particularly suited for use in conjunction with chromatographic methods, particularly those providing assays for biologically significant analytes. The devices are particularly suited for clinical assay methods including immunoassays such as radioimmunoassays, enzyme immunoassays, fluorescent immunoassays, etc.

Before proceeding further with the description of the specific embodiments of the present invention, a number of terms will be defined.

Bibulous material—a porous material having pores of at least $0.1\mu$, preferably at least $1.0\mu$, which is susceptible to traversal by a liquid medium, for example, an aqueous medium, in response to capillary force. Such materials are generally hydrophilic or hydrophobic depending on whether the liquid medium is polar or non-polar, respectively, or are capable of being rendered hydrophilic or hydrophotic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as polystyrene, polyethylene, nitrocellulose, cellulose acetate, poly(vinyl chloride), polyacrylamide, cross-linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized.

One or more of the pieces of bibulous material can be a single structure such as a sheet cut into strips or it can be several strips or particulate material bound to a support or solid surface such as found, for example, in thin-layer chromatography and may have an absorbent pad either as an integral part or in liquid contact. The piece of bibulous material can be comprised of several segments, one or more being an absorbent pad, bound to a support. The piece of bibulous material can also be a sheet having lanes thereon or capable of spotting to induce lane formation, wherein a separate assay can be conducted in each lane. The absorbent pad may be any hydrophilic bibulous material such as paper, sponge, felt, porous polymers and the like. The piece of bibulous material can have a rectangular, circular, oval, triangonal or other shape provided that there is at least one direction of traversal of a liquid test solution by capillary migration. In the following discussion, strips of bibulous material will be described by way of illustration and not limitation.

The support for the bibulous material, where a support is desired or necessary, will normally be insoluble in the liquid medium, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or, in the case where the bibulous material is used in an assay, non-specifically bind assay components, or interfere with the signal produced by the assay. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

The two pieces of bibulous material used in the present invention need not be comprised of the same bibulous substance. For example, the first piece of bibulous material can be comprised of silica whereas the second piece of bibulous material can be comprised of alumina. However, in a preferred embodiment, both pieces of bibulous material are comprised of the same bibulous substance. In some cases the first and second pieces of bibulous material may be initially joined although subject to separation when actuated. For example, in one embodiment, the first and second pieces of bibulous material are paper strips which are initially joined but have perforations or other weakening between them, which upon actuation of the device, will separate at the point of perforation or other weakening. In these cases, such pieces of bibulous material are useful in the present invention.

Liquid expandable piece of bibulous material—a piece of bibulous material which upon exposure to liquid expands in size as compared to its compressed dry state. Normally, a compressed dry state of such materials is obtained by first wetting the material, then compressing it, then drying the material while maintaining the compression. Other materials, such as swellable polymers, naturally swell when wet and shrink when dried. Preferably, upon exposure to liquid, the liquid expandable piece of bibulous material will expand its size by at least 10%; more preferably by at least 50%; and even more preferably by between 50% and 200%. However, all that is required is that the liquid expandable piece of bibulous material expand a sufficient distance so as to interrupt a capillary flow relationship between two pieces of bibulous material which theretofore were in a capillary flow relationship.

Such materials may be hydrophilic or hydrophobic depending on the liquid medium or are capable of being rendered hydrophilic or hydrophobic and include, for example, cellulosic, rubber, polyurethane and natural sponges, fibers, papers, swellable polymers, etc. The liquid expandable piece of bibulous material may have fibers, woven fabrics, or other materials included therein provided that such other materials do not alter either the bibulous or liquid expandable nature of these pieces. Where the material is not intrinsically expandable upon wetting, it may be caused to be expandable, for example, by compressing the material while saturated with a solution of a solute and drying the material in the compressed form wherein the residual solute serves to prevent reexpansion of the dry material until the solute is resolubilized by rewetting. The solute may be salts, particularly polycationic or polyanionic salts such as sulfates, polybrene, polyacrylate, etc. Additionally, carbohydrates, proteins, synthetic polymers, and a wide variety of other compounds can be used to prevent reexpansion of the dry material. The liquid expandable pieces of bibulous material can be attached to a support. On the other hand, the bibulous material may provide its own support. When a support is used, the support will normally be water insoluble, non-porous, and rigid and usually will be of the same length as the liquid expandable piece of bibulous material but need not be. A wide variety of organic and inorganic materials, both natural and synthetic, and combinations thereof, may be employed provided only that the support does not interfere with either the capillary action or the expansion of the liquid expandable piece of bibulous material. Preferably, the liquid expandable piece of bibulous material will expand preferentially in one direction, i.e., the height will increase at a much greater rate than either the length or the width. Preferred liquid expandable pieces of bibulous material are compressed regenerated cellulose sponges which when wet tend to expand in the direction of compression. Preferably, in its unactuated state, liquid expandable piece of bibulous material is completely dry.

Liquids that may be used to expand the materials can be organic or inorganic, usually solvents, and preferably polar solvents, most commonly aqueous solvent including containing 0.001 to 40% of polar organic solvents such as dimethylformamide, dioxanes, dimethyl sulfoxide, glycerol, dimethoxyethane, ethanol, and the like.

Non-capillary flow relationship—two pieces of bibulous material are in a non-capillary flow relationship when liquid is unable to move by capillarity, i.e., capillary migration, from the first piece to the second piece of bibulous material. One manner of creating a non-capillary flow relationship between two pieces of bibulous material is to prevent any contact between the pieces.

Capillary flow relationship—two pieces of bibulous material are in a capillary flow relationship when liquid is able to move by capillarity, i.e., capillary migration, from one piece to the other piece of bibulous material. One manner of creating a capillary flow relationship between two pieces of bibulous material is to allow contact between portions of the pieces which allow capillary flow from one piece to the other.

Expandable member—a member having at least two arms extending from a central shoulder and running substantially parallel to each other wherein at least one of the arms is capable of being expanded away from the other when pressure is applied along an axis running substantially perpendicular to and outward from that arm. The shoulder of the expandable member is comprised of a flexible material such as semi-rigid plastic or pliable metal which permits at least one of the arms of the expandable member to be susceptible to expansion (in the direction away from the other arm) by applied outward pressure. Generally, the flexible material should be sufficiently pliable so as to result in expansion of at least one of the arms by the pressure resulting from the expansion of a liquid expandable piece of bibulous material. In general, the two pieces of bibulous material as well as the liquid expandable piece of bibulous material are place on the arms of the compressible members in such a manner that a capillary flow relationship exists between the two pieces prior to actuation (expansion) of the liquid expandable piece of bibulous material. In turn, when the liquid expandable piece of bibulous material is expanded by exposing this piece to a sufficient amount of liquid so as to wet it, the resulting pressure on at least one of the arms results in a sufficient increase in the distance between the two arms to break the contact between the two pieces of bibulous material. This resulting break interrupts the capillary flow relationship between the two pieces of bibulous material.

Referring now to the drawings, FIG. 1A is a cross-sectional view of one embodiment of this invention in its unactuated state. In FIG. 1A, device 10 consists of an expandable member 12 having two arms 14 and 16 attached through shoulder 18. Attached to arm 14 is first piece of bibulous material 20. Attached to arm 16 is second piece of bibulous material 22. First piece of bibulous material 20 has an adjacent portion 24 which contacts adjacent portion 26 of second piece of bibulous material 22 thereby permitting a capillary flow relationship between first and second pieces of bibulous material 20 and 22. Attached to arm 14 above and separated from first piece of bibulous material 20 is a liquid expandable piece of bibulous material 28 which is also in contact with second piece of bibulous material 22 and accordingly is in a capillary flow relationship with second piece of bibulous material 22. Insofar as first and second pieces of bibulous material 20 and 22 are in a capillary flow relationship, device 10 is in its unactuated state.

FIG. 1B illustrates device 10 in its actuated state. As shown in this figure, device 10 is actuated by wetting of the liquid expandable piece of bibulous material 28 which results in its expansion. In general, liquid expandable piece of bibulous material 28 is wetted by allowing capillary flow along the first and second pieces of bibulous material 20 and 22. Because liquid expandable piece of bibulous material is in capillary flow relationship to the second piece of bibulous material 22, once capillary flow along second piece of bibulous material reaches liquid expandable piece of bibulous material 28, it will wet it.

When liquid expandable piece of bibulous material 28 is wetted, it expands and the resulting outward pressure forces arms 14 and 16 to further separate from each other which, in turn, results in adjacent portion of first piece of bibulous material 24 breaking contact with adjacent portion of second piece of bibulous material 26 thereby interrupting capillary flow between these two pieces.

In view of the above, it is readily apparent that the extent of capillary flow along second piece of bibulous material 22 is governed by the positioning of liquid expandable piece of bibulous material 28. In particular, the further up liquid expandable piece of bibulous material 28 is place along second piece of bibulous material 22, the further capillary flow will continue on second piece of bibulous material 22 prior to actuation of the liquid expandable piece of bibulous material 28. Accordingly, merely by placing liquid expandable piece of bibulous material 28 at an appropriate site along second piece of bibulous material 22, one can control the extent of capillary migration along second piece of bibulous material 22 and thus control the amount of liquid taken up by second piece of bibulous material 22.

FIG. 2A illustrates another embodiment of the present invention in its unactuated state. In this figure, device 30 comprises first piece of bibulous material 32 and a second piece of bibulous material 34 both of which partially rest on support 42. Support 42 is comprised of any material which neither interferes with the assay or test being conducted nor interferes with the capillary flow of liquid along the bibulous material. Suitable materials include glass, ceramics, metals, polymers such as polypropylene, polybutylene, polystyrene, etc. First piece of bibulous material 32 has a contact portion 36 and an adjacent portion 38; whereas second piece of bibulous material 34 has an adjacent portion 40. In the unactuated state of device 30, adjacent portion 38 contacts adjacent portion 40 thereby defining a capillary flow relationship between first and second pieces of bibulous material 32 and 34. First piece of bibulous material 32 partially rests on top surface 44 of support 42; whereas second piece of bibulous material 34 rests on top surface 46 of support 42 as well as top surface of first piece of bibulous material 32 and the top surface of liquid expandable piece of bibulous material 48. First piece of bibulous material 32, second piece of bibulous material 34, top surface 44 and top surface 46 define space 50. Space 50 provides room for liquid expandable piece of bibulous material 48 which is separated from first piece of bibulous material 32 but is in contact with and therefore in a capillary flow relationship with second piece of bibulous material 40.

FIG. 2B illustrates device 30 in its actuated state. As shown in this figure, device 30 is actuated by wetting of the liquid expandable piece of bibulous material 48 which results in its expansion. In general, liquid expandable piece of bibulous material 48 is wetted by allowing capillary flow along the first and second pieces of bibulous material 32 and 34. In particular, contact portion 36 of first piece of bibulous material 32 is placed into a liquid solution which is allowed to flow by capillarity to the second piece of bibulous material. Because liquid expandable piece of bibulous material 48 is in capillary flow relationship to second piece of bibulous material 34, once capillary flow along second piece of bibulous material reaches liquid expandable piece of bibulous material 48, it will wet it.

When liquid expandable piece of bibulous material 48 is wetted, it expands and the resulting upward pressure forces adjacent portion of second piece of bibulous material 38 to separate from adjacent portion of first piece of bibulous material 40 thereby interrupting capillary flow between these two pieces.

In view of the above, it is readily apparent that the extent of capillary flow along second piece of bibulous material 34 is governed by the positioning of liquid expandable piece of bibulous material 48. In particular, the further to the right liquid expandable piece of bibulous material 48 is place along second piece of bibulous material 34, the further capillary flow will continue on second piece of bibulous material 34 prior to actuation of the liquid expandable piece of bibulous material 48. Accordingly, merely by placing liquid expandable piece of bibulous material 48 at an appropriate site along second piece of bibulous material 34, one can control the extent of capillary migration along second piece of bibulous material 34 and thus control the amount of liquid taken up by second piece of bibulous material 34.

First piece and/or second piece of bibulous material 32 and 34 can have appropriate reagents bound at predetermined sites thereon. See, for instance, Zuk et al, U.S. Pat. No. 4,435,504; Weng et al, U.S. Pat. No. 4,740,468; and Tom et al, U.S. Pat. No. 4,366,241, each of which is incorporated herein in its entirety.

FIG. 3A illustrates still another embodiment of the present invention in its unactuated state. In this figure, device 52 comprises first piece of bibulous material 54 and a second piece of bibulous material 56 both of which partially rest on support 58. First piece of bibulous material 54 has a contact portion 60 and an adjacent portion 62; whereas second piece of bibulous material 56 has an adjacent portion 64. In the unactuated state of device 52, adjacent portion 62 contacts adjacent portion 64 thereby defining a capillary flow relationship between first and second pieces of bibulous material 54 and 56. First piece of bibulous material 54 partially rests on top surface 66 of support 58; whereas second piece of bibulous material 56 rests on top surface 68 of support 58 as well as top surface of first piece of bibulous material 54. Between top surface 66 and top surface 68 is a cavity which has a top surface 70 below either top surface 66 or top surface 68 of support 58. First piece of bibulous material 54, second piece of bibulous material 56, top surface 66, top surface 68 and top surface 70 define space 72. Space 72 provides room for liquid expandable piece of bibulous material 74 which is separated from both first piece of bibulous material 54 and second piece of bibulous material 56 and therefore is in a non-capillary flow relationship with first and second pieces of bibulous material.

FIG. 3B illustrates device 52 in its actuated state. As shown in this figure, device 52 is actuated by wetting of the liquid expandable piece of bibulous material 74 which results in its expansion. Before wetting, liquid expandable piece of bibulous material 74 is in a non-capillary flow relationship with either first or second pieces of bibulous material 54 and 56. Accordingly, liquid expandable piece of bibulous material 74 is actuated by wetting with a liquid which is not transported via capillarity through first and/or second piece of bibulous material 54 and 56. For example, sufficient liquid can be added directly to liquid expandable piece of bibulous material 74 by a pipette or syringe so as to wet it. Alternatively, space 72 may contain a breakable capsule (not shown) which contains sufficient quantity of liquid to wet liquid expandable piece of bibulous material 74. When the breakable capsule is fractured, the confined liquid is released. If necessary, the side walls of support 42 can extend upward around space 72 so as to define a chamber capable of holding a certain volume of liquid. Accordingly, when the capsule is fractured, the release liquid will be confined in this chamber along with liquid expandable piece of bibulous material 74 which is actuated by the resulting wetting of this piece. Suitable breakable capsules as well as means to break the capsule are disclosed in U.S. Ser. No. 35,562 filed Apr. 7, 1987 and entitled "Immunoassay Device" the disclosure of which is incorporated herein by reference in its entirety. In this regard, it is noted that space 72 permits sufficient room for inclusion of a breakable capsule while means to fracture this capsule can be placed above and on either side of second piece of bibulous material 56. Alternatively, means to fracture this capsule can be placed below second piece of bibulous material 56 preferably protruding inward into space 72 from one of the side walls of support 58.

When liquid expandable piece of bibulous material 74 is wetted, it expands and the resulting upward pressure forces adjacent portion 64 of second piece of bibulous material 56 to separate from adjacent portion 62 of first piece of bibulous material 54 thereby interrupting capillary flow between these two pieces. Accordingly, it is readily apparent that the extent of capillary flow along second piece of bibulous material 56 can be monitored and when desired, liquid expandable piece of bibulous material 74 can be actuated by wetting which results in interruption of the capillary flow relationship between first and second pieces of bibulous material 54 and 56.

FIG. 4A illustrates another embodiment of the present invention in its unactuated state. In this figure, device 80 comprises first piece of bibulous material 82 and a second piece of bibulous material 84 both of which partially rest on support 86. Support 86 is comprised of any material which neither interferes with the assay or test being conducted nor interferes with the capillary flow of liquid along the bibulous material. Suitable materials include glass, ceramics, metals, polymers such as polypropylene, polybutylene, polystyrene, etc. First piece of bibulous material 82 has a contact portion 88 and an adjacent portion 90; whereas second piece of bibulous material 84 has an adjacent portion 92. In the unactuated state of device 80, adjacent portion 90 contacts adjacent portion 92 thereby defining a capillary flow relationship between first and second pieces of bibulous material 82 and 84. Second piece of bibulous material 84 partially rests on top surface 94 of support 86; whereas first piece of bibulous material 82 rests on top surface 96 of support 86 as well as partly on top surface 94, of support 86 and the top surface 98 of membrane 100, which serves to control the rate of flow of liquids into liquid expandable piece of bibulous material 102. Bottom surface 104 of membrane 100 uniformly rests on top surface 106 of liquid expandable piece 102. Membrane 100 has flow resistant properties to provide for controlling the rate of flow of liquid therethrough into liquid expandable piece 102. A wide variety of compositions of known flow characteristics can be employed. Cavity 108 in support 86 is defined by walls 110, 112, and 114. Cavity 108 provides room for liquid expandable piece of bibulous material 102 which is separated from second piece of bibulous material 84 but is in contact with through the intermediacy of membrane 100 and, therefore, in a capillary flow relationship with first piece of bibulous material 82.

FIG. 4B illustrates device 80 in its actuated state. As shown in this figure, device 80 is actuated by wetting of the liquid expandable piece of bibulous material 102, which results in its expansion. In general, liquid expandable piece of bibulous material 102 is wetted by allowing capillary flow along the first and second pieces of bibulous material, 82 and 84. In particular, contact portion 88 of first piece of bibulous material 82 is contacted with a liquid solution which is allowed to flow by capillarity to the second piece of bibulous material. Contact can be achieved by placing a portion of device 80 into a liquid solution or by applying the liquid solution to device 80 by dropper, pipette, and the like. Because liquid expandable piece of bibulous material 102 is in capillary flow relationship to first piece of bibulous material 82, once capillary flow along first piece of bibulous material passes into and through membrane 100 and reaches liquid expandable piece of bibulous material 102, it will wet it.

When liquid expandable piece of bibulous material 102 is wetted, it expands and the resulting upward pressure forces adjacent portion 90 of first piece of bibulous material 82 to separate from adjacent portion 92 of second piece of bibulous material 84 thereby interrupting capillary flow between these two pieces.

The extent of capillary flow along second piece of bibulous material 84 is governed by the flow of liquid through membrane 100 and into liquid expandable piece of bibulous material 102. In particular, the more flow resistant membrane 100 is, the longer the time for liquid to pass through to liquid expandable piece of bibulous material 102, and the further capillary flow will continue on second piece of bibulous material 84 prior to actuation of the liquid expandable piece of bibulous material 102. Accordingly, merely by selecting membrane 100 of appropriate flow characteristics, one can control the extent of capillary migration along second piece of bibulous material 84 and thus control the amount of liquid taken up by second piece of bibulous material 84.

First piece and/or second piece of bibulous material 82 and 84, respectively, can have appropriate reagents bound at predetermined sites thereon. See, for instance, Zuk et al, U.S. Pat. No. 4,435,504; Weng et al, U.S. Pat. No. 4,740,468; and Tom et al, U.S. Pat. No. 4,366,241, each of which is incorporated herein in its entirety.

. FIG. 5A illustrates another embodiment of the present invention in its unactuated state. In this figure, device 120 comprises first piece of bibulous material 122, which rests on support 124, and second piece of bibulous material 126, which rests on non-porous membrane 128. Support 124 is comprised of any material which neither interferes with the assay or test being conducted nor interferes with the capillary flow of liquid along the bibulous material. Suitable materials include glass, ceramics, metals, polymers such as polypropylene, polybutylene, polystyrene, etc. First piece of bibulous material 122 has a contact portion 130 and an adjacent portion 132; whereas second piece of bibulous material 126 has an adjacent portion 134. In the unactuated state of device 120, adjacent portion 132 contacts adjacent portion 134, thereby defining a capillary flow relationship between first and second pieces of bibulous material 122 and 126. The bottom surface 136 of first piece of bibulous material 122 rests on top surface 138 of support 124; whereas the bottom surface 140 second piece of bibulous material 126 rests on top surface 142 of membrane 128. The bottom surface 144 of membrane 128 rests on the top surface 146 of liquid expandable piece of bibulous material 148. Membrane 128 and liquid expandable piece of bibulous material 148 are recessed in support 124. Adjacent second piece of bibulous material 126, membrane 128 and liquid expandable piece 148 is third piece of bibulous material 150. The bottom surface 152 of third piece 150 rests on top portion 154 of support 124, as does the bottom 156 of liquid expandable piece of bibulous material 148, which is separated from first piece of bibulous material 122. Liquid expandable piece of bibulous material 148 is in contact with and therefore in a capillary flow relationship with third piece of bibulous material 150 by virtue of piece 150 being in capillary flow relationship with second piece of bibulous material 126.

FIG. 5B illustrates device 120 in its actuated state. As shown in this figure, device 120 is actuated by wetting of the liquid expandable piece of bibulous material 148 which results in its expansion. In general, liquid expandable piece of bibulous material 148 is wetted by allowing capillary flow along the first piece of bibulous material 122. In particular, contact portion 130 of first piece of bibulous material 122 is contacted with a liquid solution which is allowed to flow by capillarity to second piece of bibulous material 126 and to third piece of bibulous material 150. Because liquid expandable piece of bibulous material 148 is in capillary flow relationship to third piece of bibulous material 150, once capillary flow along second piece of bibulous material 126 reaches third piece of bibulous material 150 and ultimately liquid expandable piece of bibulous material 148, it will wet it.

When liquid expandable piece of bibulous material 148 is wetted, it expands and the resulting upward pressure forces membrane 128 and adjacent portion 134 of second piece of bibulous material 126 upward, thereby separating 126 from adjacent portion 132 of first piece of bibulous material 122 and interrupting capillary flow between these two pieces.

In view of the above, it is readily apparent that the extent of capillary flow along second piece of bibulous material 126 is governed by the positioning of size and liquid holding capacity of third piece of bibulous material 150. In particular, the larger third piece of bibulous material 150, the more capillary flow will continue on second piece of bibulous material 126 prior to actuation of the liquid expandable piece of bibulous material 148.

First piece and/or second piece of bibulous material 122 and 126 can have appropriate reagents bound at predetermined sites thereon. See, for instance, Zuk et al, U.S. Pat. No. 4,435,504; Weng et al, U.S. Pat. No.

4,740,468; and Tom et al, U.S. Pat. No. 4,366,241, each of which is incorporated herein its entirety.

In view of the above, it is apparent that devices of the present invention allow interruption of a capillary flow relationship between two pieces of bibulous material which theretofore were in a capillary flow relationship. Such devices have the particular advantage of permitting interruption of the capillary flow relationship between two or more pieces of bibulous material with little or no operator involvement.

The dimensions of the devices of the present invention can vary depending upon the particular use, that is, whether the devices are used in immunoassays, etc. For example, the positioning of the liquid expandable piece of bibulous material can vary from one assay to another so as to permit the uptake of different amounts of liquid prior to interruption of the capillary flow relationship. Likewise, the extent of expansion of the liquid expandable piece of bibulous material depends on factors such as whether this piece is contacting or not contacting either the first or second piece of bibulous material. Obviously, if the liquid expandable piece of bibulous material is not contacting either the first or second piece of bibulous material, it will need to expand more than a liquid expandable piece of bibulous material which is placed in the same position but which contacts either the first or second piece of bibulous material. Those skilled in the art will be able to construct devices of the present invention having appropriate dimensions in view of the disclosure herein.

The devices of the present invention can be incorporated into a suitable housing to facilitate their use in certain assays and tests. When a housing is used, it (as well as the support) should be prepared from non-corrosive materials which do not readily degrade or disintegrate upon exposure to the solutions employed in the assay. Additionally, such materials should not interfere with the assay being conducted. In general, metals, metal alloys, glass and rigid and semi-rigid plastic can be used. Preferably, a rigid or a semi-rigid plastic is employed. As used herein, the term "non-corrosive" means that the material is not subject to undo decomposition or disintegration when routinely used in the devices of the present invention.

The devices of the present invention can be employed to determine, for example, the result of a chemical test particularly by employing a chromatographic step. The present device can find application in a method for determining qualitatively and/or quantitatively the presence or amount, respectively, of an analyte in a sample suspected of containing the analyte. Examples of such methods are described in U.S. Pat. Nos. 4,366,241; 4,740,488; 4,168,146 and 4,435,504, the disclosures of which are incorporated herein by reference and the terms used below have the meanings set out therein.

The above methods may be carried out on, among others, a bibulous strip, as stationary solid phase and involving a moving liquid phase. The stationary solid phase can be contacted with a plurality of reagents in a number of different solutions.

Referring to FIG. 1A for an assay for analyte a member of specific binding pair (sbp member) can be non-diffusively bound to a bibulous strip to form an "immunosorbing zone" which may be all or a portion of first piece of bibulous material 20. The analyte from the sample traverse piece 20 being carried along with a solvent whose front crosses the zone. The analyte, which may be the homologous or reciprocal sbp member to the sbp member bound to the support, becomes bound to the support through the intermediacy of sbp member complex formation. The signal producing system provides the manner by which part or all of the area in the immunosorbing zone to which the analyte is bound may be distinguished from the area in which it is absent.

The incremental movement of the sample through the immunosorbing zone results from dissolving the sample in an appropriate solvent and the transport of the solution through the immunosorbing zone due to capillarity.

The solvent is normally an aqueous medium, which may be up to about 40 weight percent of other polar solvents, particularly oxygenated solvents of from 1 to 6, more usually of from 1 to 4 carbon atoms, including alcohols, ethers and the like. Usually, the co-solvents are present in less than about 20 weight percent.

The pH for the medium is usually in the range of 4–11, more usually 5–10, and preferably in the range of about 6.5–9.5. The pH is chosen to maintain a significant level of binding affinity of the sbp members. Various buffers may be used to achieve the desired pH and maintain the pH during the elution. Illustrative buffers include borate, phosphate, carbonate, tris, barbital and the like. The particular buffer employed is not critical, but in individual assays, one buffer may be preferred over another.

Moderate, and desirably substantially constant, temperatures are normally employed for carrying out the assay. The temperatures for the chromatography and production of a detectable signal are generally in the range of about 10°–50° C., more usually in the range of about 15°–50° C., and frequently are ambient temperatures, that is, about 15°–25° C.

The concentration of analyte which may be assayed generally varies from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions are generally determined by the concentration range of interest of the analyte, the final concentration of each of the reagents is normally determined empirically to optimize the sensitivity of the assay over the range of interest. However, with certain protocols, individual regents may be used in substantial excess without detrimentally affecting the sensitivity of the assay.

Other reagents which are members of the signal producing system can vary widely in concentration depending upon the particular protocol and their role in signal production.

In carrying out the assay, the protocol normally involves dissolving the sample into the eluting solvent. The sample may be derived from a wide variety of sources, such as physiologic fluids, illustrated by blood, serum, plasma, urine, ocular lens fluid, spinal fluid, etc., chemical processing streams, food, pesticides, pollutants, etc.

The bottom or proximal end of device 10 (i.e., the end of device 10 that is contacted with the liquid medium) is then contacted with the sample dispersed in the solvent, which is normally a buffered aqueous medium which may contain one or more members of the signal producing system. Where a member of the signal producing system is present, at least one member is conjugated to a sbp member to provide a sbp member-label conjugate.

Sufficient time is allowed for the solvent front to complete traversal of first piece of bibulous material 20 containing the immunosorbing zone.

For the most part, relatively short times are involved. Usually, the traverse of the sample through the immunosorbing zone on first piece 20 takes at least 30 sec and not more than 1 hour, more usually from about 1 min to 30 min. The development of the signal generally ranges from 30 sec to 30 min, more usually from about 30 sec. to 5 min.

Solutions of other reagents including signal producing system members not included with the sample solution or on piece 20 are then contacted with device 10. These solutions are allowed to migrate along first piece of bibulous material 20 and subsequently along second piece of bibulous material 22. The length of piece 22 and its relationship with liquid expandable piece of bibulous material 28 determine when contact at points 24 and 26 is broken by expansion of 28. This in turn determines how much liquid from the sample and reagent solution is taken up by device 10. At that time the immunosorbing zone is examined for the presence of signal.

For quantitative assays, a standard sample is provided having a known amount of analyte. The analyte sample and the standard are run at the same time each on a different device 10, and a quantitative comparison is made between the standard sample and the analyte sample. If necessary, more than one standard is employed, so that the distance traversed can be graphed for the different concentrations and used to quantitate a particular sample.

To enhance the versatility of the subject invention, the device can be provided in packaged combination with a liquid medium and other components in the same or separate containers as the interreactivity of the components permit. For conducting an assay the kit can further include other separately packaged reagents for conducting an assay including members of the signal producing system, antibodies either labeled or unlabeled, supports, ancillary reagents, and so forth. Reagents can be provided so that the ratio of the reagents provides for substantial optimization of the method and assay.

Having described several embodiments of devices and methods of the present invention by way of example and not limitation, it is to be understood that various changes in form and detail may be made therein without departing from the scope and spirit of this invention or the scope of the appended claims.

What is claimed is:

1. A capillary flow device which comprises:
   (a) first and second pieces of bibulous material each positioned on a support, said first and second pieces being in a capillary flow relationship to each other; and
   (b) a liquid expandable piece of bibulous material positioned on a support so as to force said first and second pieces of bibulous material out of said capillary flow relationship to each other when said liquid expandable piece of bibulous material is wetted and expanded.

2. The device according to claim 1 wherein said liquid expandable piece of bibulous material is in a capillary flow relationship to said second piece of bibulous material.

3. The device according to claim 1 wherein said liquid expandable piece of bibulous material in its unexpanded state is in a non-capillary flow relationship with said first and second pieces of bibulous material.

4. The device according to claim 1 wherein said first and second pieces of bibulous material are not expandable.

5. The device according to claim 1 wherein said first and second pieces are on the same support.

6. The device according to claim 1 wherein said first and second pieces of bibulous material contact each other.

7. The device according to claim 6 wherein said liquid expandable piece of bibulous material expands when wetted and thereby forces said first and second pieces of bibulous material out of contact with each other.

8. The device according to claim 1 wherein said first and second piece of bibulous material are paper strips.

9. The device according to claim 8 wherein said liquid expandable piece of bibulous material is an expandable sponge.

10. A method for interrupting capillary flow of a liquid between first and second pieces of bibulous material which prior to actuation are in a capillary flow relationship to each other which comprises:
    (a) providing a device which comprises (i) first and second pieces of bibulous material each positioned on a support, each of said first and second pieces having adjacent and non-adjacent portions wherein said adjacent portions are in capillary flow relationship to each other, and (ii) a liquid expandable piece of bibulous material positioned on a support;
    (b) contacting said non-adjacent portion of said first piece of bibulous material with a liquid and allowing said liquid to traverse by capillarity through at least a portion of said second piece of bibulous material; and
    (c) allowing a liquid to contact said liquid expandable piece of bibulous material whereupon said liquid expandable piece of bibulous material expands and forces said adjacent portions of said first and second pieces of bibulous material out of capillary flow relationship to each other.

11. The method according to claim 10 wherein said first and second pieces of bibulous material are not expandable.

12. The method according to claim 10 wherein said first and second piece of bibulous material are paper strips.

13. The method according to claim 10 wherein said first and second pieces of bibulous material are on the same support.

14. The method according to claim 10 wherein said liquid expandable piece of bibulous material is an expandable sponge.

15. The method according to claim 14 wherein said expandable sponge is a compressed regenerated cellulose sponge.

16. The method according to claim 10 wherein said liquid expandable piece of bibulous material is in a capillary flow relationship to said second piece of bibulous material.

17. The method according to claim 16 wherein said liquid which traverses at least a portion of said second piece of bibulous material is allowed to traverse by capillarity through at least that portion of said second piece of bibulous material which is in capillary flow relationship to said liquid expandable piece of bibulous material.

18. The method according to claim 10 wherein said liquid expandable piece of bibulous material in its unexpanded state is in a non-capillary flow relationship with said first and second pieces of bibulous material.

19. The method according to claim 18 wherein said liquid for contacting said liquid expandable piece of bibulous material is external to said liquid flowing by capillarity along said first and second pieces of bibulous material.

20. The method according to claim 10 wherein said first and second pieces of bibulous material contact each other.

21. The method according to claim 20 wherein said liquid expandable piece of bibulous material expands when wetted and thereby forces said first and second pieces of bibulous material out of contact with each other.

22. A method for interrupting capillary flow of a liquid between first and second pieces of bibulous material which prior to actuation are in a capillary flow relationship to each other which comprises:
(a) contacting a portion of a first piece of bibulous material with a liquid, said portion being non-adjacent to a portion of second piece of bibulous material wherein said first and second pieces of bibulous material each have adjacent and non-adjacent portions and wherein said adjacent portions are in capillary flow relationship to each other;
(b) allowing said liquid to traverse by capillarity through at least a portion of said second piece of bibulous material; and
(c) allowing a liquid to contact a liquid expandable piece of bibulous material whereupon said liquid expandable piece of bibulous material expands and forces said adjacent portions of said first and second pieces of bibulous material out of capillary flow relationship to each other.

23. The method according to claim 22 wherein said first and second pieces of bibulous material are not expandable.

24. The method according to claim 22 wherein said first and second piece of bibulous material are paper strips.

25. The method according to claim 22 wherein said first and second pieces of bibulous material are on a support.

26. The method according to claim 22 wherein said liquid expandable piece of bibulous material is in a capillary flow relationship to said second piece of bibulous material.

27. The method according to claim 26 wherein said liquid which traverses at least a portion of said second piece of bibulous material is allowed to traverse by capillarity through at least that portion of said second piece of bibulous material which is in capillary flow relationship to said liquid expandable piece of bibulous material.

28. The method according to claim 22 wherein said liquid expandable piece of bibulous material in its unexpanded state is in a non-capillary flow relationship with said first and second pieces of bibulous material.

29. The method according to claim 28 wherein said liquid for contacting said liquid expandable piece of bibulous material is external to said liquid flowing by capillarity along said first and second pieces of bibulous material.

30. The method according to claim 22 wherein said first and second pieces of bibulous material contact each other.

31. The method according to claim 30 wherein said liquid expandable piece of bibulous material expands when wetted and thereby forces said first and second pieces of bibulous material out of contact with each other.

32. The method according to claim 22 wherein said liquid expandable piece of bibulous material is an expandable sponge.

33. The method according to claim 32 wherein said expandable sponge is a compressed regenerated cellulose sponge.

34. A kit comprising in packaged combination:
(a) a capillary flows device which device comprises:
(i) first and second pieces of bibulous material each postioned on a support, said first and second pieces being in a capillary flow relationship to each other; and
(ii) a liquid expandable piece of bibulous material positioned on a support so as to force said first and second pieces of bibulous material out of said capillary flow relationship to each other when said liquid expandable piece of bibulous material is wetted and expanded, and
(b) a liquid meduim.

* * * * *